United States Patent [19]

Stöhr et al.

[11] 4,005,704
[45] Feb. 1, 1977

[54] DEVICE FOR THE FOOT END OF A LEG CAST

[76] Inventors: Christoph Stöhr, Eisenstr. 2; Klaus Kerkrath, Tannenweg 3, both of 6619 Losheim, Germany

[22] Filed: Sept. 3, 1975

[21] Appl. No.: 609,955

[30] Foreign Application Priority Data

Sept. 11, 1974 Germany .......................... 2443416
Feb. 17, 1975 Germany .......................... 047573

[52] U.S. Cl. ................................................ 128/83.5
[51] Int. Cl.² .......................................... A61F 5/04
[58] Field of Search ............. 128/82, 83.5, 83, 581, 128/80 R; 36/4, 7.1 R, 7.3

[56] References Cited

UNITED STATES PATENTS

| 2,032,052 | 2/1936 | Friedenberg | 36/7.3 |
| 2,278,626 | 4/1942 | Vasko | 128/83.5 |
| 3,545,104 | 12/1970 | Laurie | 128/83.5 |
| 3,800,376 | 4/1974 | Whyte | 128/83.5 |
| 3,802,424 | 4/1974 | Newell | 128/82 |

*Primary Examiner*—Lawrence W. Trapp
*Attorney, Agent, or Firm*—Fidelman, Wolffe & Waldron

[57] ABSTRACT

A foot or leg cast comprising a cast boot with a flexible overshoe, the latter being removable from the former at will and being preferably constructed of rubber with reinforced edges, inclined side walls and a rolled sole which includes a flat line diagonal to the longitudinal axis of the foot.

6 Claims, 3 Drawing Figures

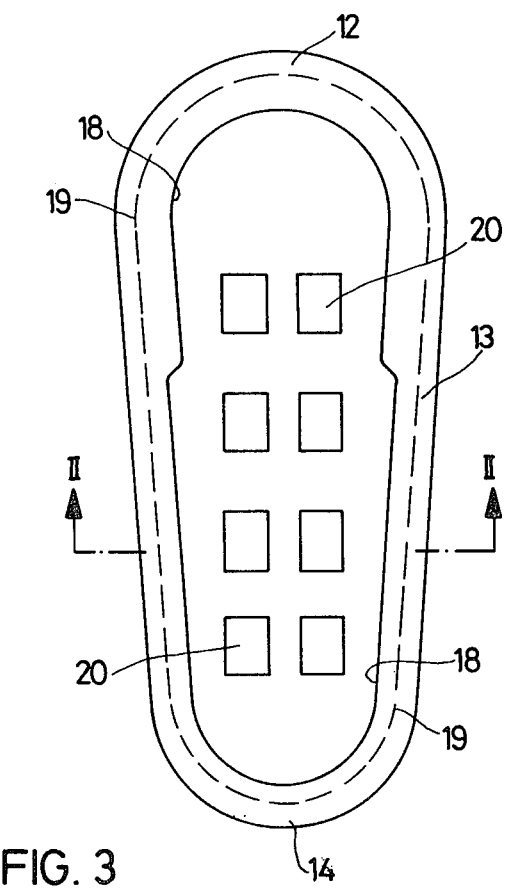

DEVICE FOR THE FOOT END OF A LEG CAST

The invention relates to a device for the foot end of a leg cast. In the case of broken legs or the like, leg casts are often applied to give the patient back his mobility. In order not to be completely dependent on the constant use of crutches, the patient must be able to place the leg in the cast on the floor.

The normal procedure to make this possible is to plaster a cast support right into the cast. Instead of this, it is also possible just to plaster a mounting into the cast, to which a detachable supporting device can be attached. The cast support, the attachment device or similar devices are plaster-fixed by means of cementing with plaster at the upper or lower leg. The should fulfill their function as a brace for the entire period during which the patient must wear the cast.

Known cast braces have various disadvantages. First of all, they normally represent a fixed point of support, restricted in its square dimensions and in its location. Such a brace produces a tiring and awkward way of walking, which is especially difficult on uneven surfaces, or in climbing stairs. Because of the portion of the brace that projects beyond the sole of the cast, driving a car is almost impossible with such a cast, thus further restricting the patient's mobility.

The most essential disadvantage, however, in the case of all the braces and supporting devices plastered into the cast, is the fact that great stress is applied to points of the cast sole or certain other areas of the cast. This stress often leads to penetration and consequent breaking of the cast within as little as two weeks. Thus the requirement that the device attached to the cast should have the same life's duration as the cast itself is not fulfilled. The consequences are the discomfort of the patient and setbacks in the healing process due to unfavorable stress on the cast and necessary repairs. In certain cases, the whole cast must be replaced because of its partial destruction.

Another disadvantage of the known devices consists in the fact that the parts worked into the plaster project through the sole of the cast and present an obstacle in lying down, going to bed, etc. Also, these projecting parts are in constant contact with the floor, and must be repeatedly washed, e.g. before retiring. This is nearly impossible for the patient to do himself, and in any case presents problems.

A final disadvantage consists in the fact that the plastering of the detachable parts and the application of the additional plaster this requires causes a considerable increase in weight of the cast, which the patient must bear constantly, and not only when walking. It is considered most favorable to keep the cast as light as possible, while at the same time insuring the greatest degree of sturdiness possible.

It is the object of the invention to propose a device that facilitates walking with a cast, without necessitating that any parts be plastered directly into the cast.

The invention solves this problem in that it is constructed as a cast boot with a flexible overshoe that can be placed over the cast and removed from it at will.

We can see first of all that such a cast boot can be pulled directly over the foot end of the cast. Any additional plaster-fixing or cast supports are not necessary. The flexible overshoe, furthermore, securely encloses the foot end of the cast, and thus attaches the cast boot to the cast. The latter is then protected against soling, as is the possibly exposed foot. The cast boot can also be easily removed before retiring. Once removed, the boot can easily be cleaned. The rolled sole of the cast boot completely replaces, when walking, the mobility of the ankle, stiffened by the cast. This insures that the patient walks with greater certainty, particularly on uneven ground or when climbing stairs. The rolled sole furthermore makes it possible for the patient to drive a car in spite of the cast. The physiologically accurate rolling of the sole thus is of great assistance to the patient. Furthermore, the strength is transferred from the brace point on the floor to the greater surface of the cast sole. Great point stress is thus avoided, the cast withstands the stress applied to it well, and lasts for the entire duration for which it was meant to be worn. Furthermore, the clever combination of flexible overshoe and rolled sole makes it possible to cover the range of shoe sizes from 34 to 45 with only two different boot sizes. This reduces the cost of manufacture. In summary, we can say that the cast boot of a flexible overshoe and rolled sole offers considerable advantages to both patients and hospitals at relatively low cost. Successful application of the cast boot seems possible above all in the fields of orthopedics, surgery and traumatology.

In the following, the invention will be described with reference to the drawings.

FIG. 2 shows a cross-section along line II—II of FIG. 3, and FIG. 3 shows a top view of the cast boot.

Figure 1:
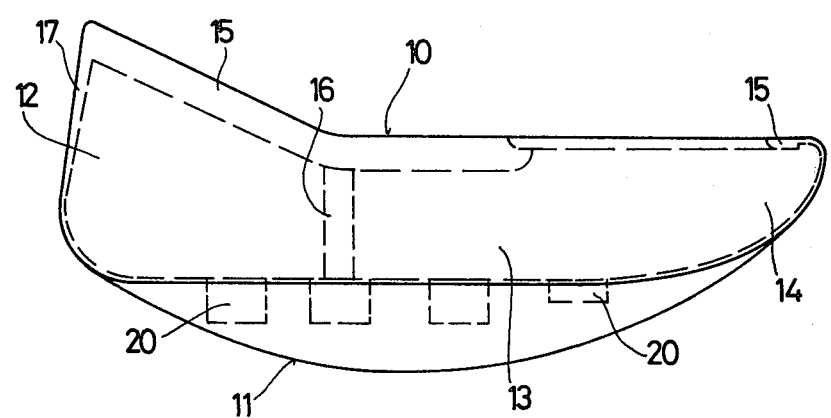
FIG. 1 shows a side view of a cast boot.

FIG. 1 shows the basic construction of the cast boot. This consists of an overshoe 10 and a rolled sole 11. The cast boot is prefereably produced in one piece. Rubber is a particularly suitable material. In any case, a flexible material is necessary, particularly because of the overshoe 10, which must be pliable.

The flexible overshoe 10 consists of a high heel envelopment 12, side walls 13 inclined inward (see also FIG. 2), and a pointed tip 14 as in a pointed shoe. The overshoe has reinforced rubber edges 15, which makes possible particularly secure attachment to the cast. Moreover, a reinforcement 16 on the sides and a reinforcement 17 in the heel, made of reinforced rubber edges, continue down into the sole. Along with the reinforced rubber edges 15, these reinforcements stretch the thin rubber walls of the overshoe, making it easier to draw it over the cast boot, but not in any way affecting the elastic properties of the overshoe 10. Due to the inward-inclinded side walls 13 and the consequently also inward-inclined heel envelopment 12, the upper inner edge 18 (see FIG. 3) of the overshoe projects over the outer edge 19 of the inner sole on all sides. This strengthens the stretching effect upon drawing on the plaster cast boot, and reinsures firm attachment of the cast boot onto the cast.

The rolled sole 11 looks like an arc or curved line from the side, connecting the heel envelopment 12 with the point 14 of the cast boot. This curved line produces a rolling effect upon walking with the cast, said effect being physiologically desirable, and far superior, in terms of certainty of step and effects on the plaster, to walking with a cast support or brace. In order to provide a sufficient standing surface, the rolled sole 11 is flat on a diagonal to the longitudinal axis of the cast boot or the foot (see FIG. 2). This construction supports the rolling movement in longitudinal direction, and at the same time provides a greater standing surface. When a flexible material, such as rubber, is used for the production of this boot, an increase in the standing surface can be achieved, especially in the case of sectioning the floor surface of the rolled sole, by a lesser compression of the rolled sole 11.

On the side of the sole that faces the sole of the foot, the rolled sole has small air chambers 20. These air chambers can be arranged next to each other in one row or, as in the form of construction shown, in two rows. They can be of various depths, and are preferably deepest where the rolled sole 11 is highest. The air chambers 20 divide the rubber mass of the rolled sole in sich a way that it can better adapt to unevennesses in the ground and can more effectively buffer against bumps and blows. Thus, this construction, too, contributes to the patient's comfort.

FIGS. 2 and 3 show that the structure of the cast boot is symmetrical with relation to its logitudinal axis. The cast boot is therefore suited to wearing on both the left and the right foot. Because of the construction of the overshoe as described above, one cast boot can fit a wide range of foot sizes. Two sizes of cast boots thus are sufficient for all cases, which makes storage much easier.

We claim:

1. A device for the foot end of a leg cast comprising a flexible overshoe adapted to be removably placed over the foot end of the cast, said overshoe having a rolled sole bounded in the longitudinal direction by a downwardly curved line extending from the heel portion to the tow portion of said overshoe and being flat in the transverse direction, said rolled sole having an anti-slip section on the surface which comes into contact with the ground and further having air chambers recessed into the surface which comes into contact with the cast-covered sole of the foot, said chambers forming at least one row in the longitudinal direction with the depth of the chambers at the ends of the row being less than those in the portion where the rolled sole is high.

2. A device according to claim 1, wherein the flexible overshoe is made of rubber.

3. A device according to claim 2, wherein the overshoe has reinforced rubber edges.

4. A device according to claim 3, wherein the flexible overshoe is of one-piece construction.

5. A device according to claim 1, wherein the side walls of the overshoe are inclined inward.

6. A device according to claim 1, wherein the flexible overshoe is constructed symmetrically with relation to its longitudinal axis.

* * * * *